US006268127B1

(12) United States Patent
Bergmeyer et al.

(10) Patent No.: US 6,268,127 B1
(45) Date of Patent: Jul. 31, 2001

(54) METHOD FOR PREPARING DNA FROM SERUM AND PLASMA

(75) Inventors: Lynn Bergmeyer, Rochester; Kerry Lee Angie, Marion, both of NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 0 days.

(21) Appl. No.: 09/493,352

(22) Filed: Jan. 28, 2000

Related U.S. Application Data
(60) Provisional application No. 60/118,496, filed on Feb. 3, 1999.

(51) Int. Cl.[7] .................................................. C12Q 1/68
(52) U.S. Cl. .............................. 435/5; 435/6; 435/91.1; 435/91.2; 435/325; 435/252.3; 435/243; 536/231
(58) Field of Search ........................... 435/5, 6, 91.1, 435/91.2, 325, 252.3, 243; 536/23.1

(56) References Cited

U.S. PATENT DOCUMENTS

| 5,089,233 | 2/1992 | DeVaney, Jr. et al. | 422/99 |
| 5,229,297 | 7/1993 | Schinpelsky et al. | 436/94 |
| 5,380,489 | 1/1995 | Sutton et al. | 422/68.1 |
| 5,582,988 | 12/1996 | Backus et al. | 435/6 |
| 5,639,599 | 6/1997 | Ryder et al. | 435/5 |

OTHER PUBLICATIONS

Henrard et al, Transfusion, vol. 33 No. 5. pp. 405–408, May 1993.*
Nolte et al., 1995, *J. Clin. Microbiol.* 33:1263–66.
Hansen et al., 1994, *J. Infect. Dis.* 170:1271–4.
Patel et al., 1994, *J. Clin. Microbiol.* 32:1431–4.
Wolf et al., 1993, *Transplanatation,* 56:330–4.
Spector et al., 1992, *J. Clin. Microbiol.* 30:2359–65.

* cited by examiner

*Primary Examiner*—W. Gary Jones
*Assistant Examiner*—Janell E. Taylor
(74) *Attorney, Agent, or Firm*—Darby & Darby

(57) ABSTRACT

Described herein are methods for extracting DNA from serum or plasma, comprising contacting serum or plasma with alkali to yield alkalinized serum or plasma, heating the alkalinized serum or plasma to a temperature ranging from about 100 to about 110° C. for a time ranging from about 5 to about 20 minutes, centrifuging the heated alkalinized serum or plasma to yield a DNA-containing supernatant, allowing the heated alkalinized serum or plasma to cool to room temperature, or about 25° C., and recovering the DNA-containing supernatant. Also disclosed are methods for detecting a DNA-containing microorganism in serum or plasma.

16 Claims, No Drawings

METHOD FOR PREPARING DNA FROM SERUM AND PLASMA

This application claims benefit to U.S. provisional application Ser. No. 60/118,496, filed Feb. 3, 1999.

FIELD OF THE INVENTION

The present invention pertains to methods for preparing DNA from serum and plasma, particularly for use as a target in amplification reactions.

BACKGROUND OF THE INVENTION

Technology is rapidly advancing in the area of amplification and detection of nucleic acids, particularly as it relates to commercial diagnostic tests, which offer early detection of infectious diseases, cancer and genetic disorders. Highly sophisticated techniques for the amplification of minute quantities of nucleic acids, such as PCR (polymerase chain reaction), are now well known (see. U.S. Pat. Nos. 4,683, 195; 4,683,202; and 4,965,188). The inherent sensitivity of PCR, i.e., its ability to amplify very small concentrations of a target DNA, means that low level carryover of PCR products, and contamination between specimens, can yield false positive results. Carryover and sample contamination, among other things, are a function of the number of manipulations of the sample required during processing. Therefore, a simple procedure with a minimal number of steps that expose the sample to the environment is highly desirable.

Traditionally, PCR identification of viremia due to infectious human cytomegalovirus (HCMV), and identification of other viruses and bacteria has been performed on peripheral blood leukocytes (WBCs) obtained from whole blood. Separation of WBCs from whole blood is usually required prior to extraction of the HCMV DNA from the WBCs. Procedures for this separation include erythrocyte sedimentation in a dextran solution (Rasmussen et al., *J. Infect. Dis.* 171:17714 82, 1995), differential lysis using ammonium chloride solutions (U.S. Pat. No. 5,702,884 Ekeze et al), or the use of commercially available procedures (such as, e.g., CPT-Vacutainer™ tubes from Becton-Dickinson). Typically, these procedures include a wash step which results in the removal of potential inhibitors of amplification; alternatively, the isolation of WBCs serves to remove these inhibitors, which typically reside in high concentration in plasma or serum.

Once the WBCs have been isolated, they are lysed and the DNA is extracted. This involves procedures such as, for example, boiling, sonication, or freeze-thawing of the WBCs, or the use of proteolytic enzymes and/or surfactants to lyse the cells and extract the DNA. DNA extraction may also involve an alkali lysis step (U.S. Pat. No. 5,639,599). Often, a more rigorous extraction/purification is performed to further ensure that purified DNA is obtained devoid of potential inhibitors, including, e.g., use of glass beads (Gene Clean II kits, Bio 101, Inc.), phenol-chloroform extraction procedures, polymer capture (U.S. Pat. No 5,582,988), spin-column adsorption (Qiagen QIAamp kits), and other commercially available DNA isolation kits (Puregene, Gentra Systems Inc.).

Notably, procedures used for isolating and lysing WBCs, which serve to wash or remove potential inhibitors from the WBC preparation, cannot be used with plasma and serum. As the vast majority of endogenous biochemical substances and consumed drugs, metabolites of drugs, and the like, reside and are heavily concentrated in serum and plasma, there is a need in the art for a rapid and robust procedure that could be used with serum and plasma which would remove the potential inhibitors or render them ineffective.

Extracellular HCMV nucleic acid in infected individuals is present in plasma and serum. Serum and plasma are gaining acceptance as samples of choice for detecting HCMV nucleic acid using PCR. Generally, the target DNA does not exist as free DNA but rather as a complex association of DNA, RNA, and proteins. The DNA must be extracted from the complex and denatured in order to render it available for amplification. Serum and plasma samples are typically subjected to heat, surfactants, and treated with proteases. Often additional rigorous protocols are employed to extract the target DNA, such as those described above for WBCs (Spector et al., *J. Clin. Microbiol.*30:2359–65, 1992; Nolte et al., *J. Clin. Microbiol.* 33:1263–66, 1995; Wolf et al., *Transplantation* 56:330–4, 1993; Patel et al., *J. Clin. Microbiol.* 32:1431–4, 1994). Alkali treatment has also been used. However, this alkali treatment typically requires a high NaOH concentration followed by a neutralization step (Hansen et al., *J. Infect. Dis.* 170:1271–4, 1994).

Thus, there is a need in the art for a rapid and efficient procedure for extracting DNA from serum and plasma that is compatible with PCR amplification methods.

SUMMARY OF THE INVENTION

The present invention provides a method for extracting DNA from serum or plasma samples. The method comprises:

(i) contacting the serum or plasma with alkali to yield alkalinized serum or plasma;

(ii) heating the alkalinized serum or plasma to a temperature between about 100 and about 110° C. for a time between about 5 and about 20 minutes, (iii) centrifuging the heated alkalinized serum or plasma; and (iv) recovering the DNA-containing supernatant.

In a preferred aspect, prior to centrifuging the heated alkalinized serum or plasma, the heated alkalinized serum or plasma produced by step (ii) is cooled or is allowed to cool to room temperature, i.e., about 25° C., prior to centrifugation in step (iii).

In another aspect, the invention provides a method for detecting the suspected presence of a DNA-containing microorganism, for example human cytomegalovirus (HCMV), in serum or plasma. The method comprises:

(i) contacting the serum or plasma with alkali to yield alkalinized serum or plasma;

(ii) heating the alkalinized serum or plasma to a temperature between about 100 and about I 110° C. for a time between about 5 and about 20 minutes;

(iii) centrifuging the heated alkalinized serum or plasma;

(iv) recovering the DNA-containing supernatant;

(v) subjecting the DNA in the supernatant to amplification using oligonucleotide primers that recognize sequences within microorganism DNA, to form microorganism-specific amplification products; and (vi) detecting the amplification products, wherein detection of amplification products specific to the microorganism indicates the presence of the microorganism in the serum or plasma.

In a preferred aspect, subsequent to step (ii), the heated alkalinized serum or plasma is cooled or is allowed to cool to room temperature, i.e., about 25° C., prior to centrifugation in step (iii).

DETAILED DESCRIPTION OF THE INVENTION

The present invention provides a simple, rapid, and highly effective method for extracting DNA from serum and plasma samples which results in DNA preparations suitable for subsequent detection assays without further manipulation.

The method comprises the steps of:

(i) contacting the serum or plasma with alkali to yield alkalinized serum or plasma;

(ii) heating the alkalinized serum or plasma to a temperature between about 100 and about 110° C. for a time between about 5 and about 20 minutes;

(iii) centrifuging the heated alkalinized serum or plasma; and (iv) recovering the DNA-containing supernatant.

It is preferred that subsequent to heating and prior to centrifugation, the heated alkalinized serum or plasma is cooled or is allowed to cool to room temperature, i.e., about 25° C. The cooling can be passive, i.e., by simple equilibration with room air, or active, i.e., the heated alkalinized serum or plasma can be refrigerated, placed on ice, or put in a water bath, until the temperature of the heated alkalinized serum or plasma reaches room temperature.

In practicing the present invention, the suitable alkali includes, but is not limited to, sodium hydroxide, potassium hydroxide, ammonium hydroxide, or a mixture of any of the foregoing. Preferably, sodium hydroxide is used. The final concentration of alkali in the mixture prepared in step (i) ranges from about 10 to about 90 mM, and most preferably from about 15 to about 50 mM. Special notice is made of an alkali concentration of about 20 mM. A preferred method involves forming a mixture of 1 part by volume of serum or plasma with about 4 parts by volume of an aqueous solution of about 25 mM alkali.

The temperature to which the alkalinized serum or plasma is heated preferably is about 105° C. and the time preferably is about 5 minutes. The centrifugation step is preferably carried out at ambient temperature for about 2 minutes at about 16,000X g.

The recovered supernatant from the centrifuged mixture can be added directly to a PCR amplification admixture. However, the supernatant can be modified by further treatment or addition of reagents as desired prior to addition to the PCR admixture. Treatment with alkali according to the invention serves to inactivate PCR inhibitors and denature proteins, particularly nucleases that can degrade the target DNA to a point where it cannot be amplified. It also serves to denature the DNA, making it more amenable to hybridization to amplification primers and thus to PCR amplification. In addition, the simplicity of the method greatly reduces the probability of sample-to-sample contamination and PCR product carryover. It also eliminates the need for costly and often unstable materials used routinely for nucleic acid isolation and purification.

The present invention is useful in preparing DNA samples for diagnostic assays, particularly those that detect DNA viruses such as, e.g., cytomegalovirus, herpes simplex virus, Epstein-Barr virus, Hepatitis B virus and any blood-borne bacteria. Detection methods in which the DNA preparations can be used include, without limitation, any method involving hybridization, including, e.g., polymerase chain reaction, ligase chain reaction, and the like. Thus, the present invention encompasses methods for the detection of DNA-containing microorganisms which comprises alkalinizing serum or plasma from a subject, heating the alkalinized serum or plasma to between about 100 and about 110° C. for a time period ranging from about 5 to about 20 minutes, centrifuging to obtain a DNA-containing supernatant, recovering the supernatant, amplifying the DNA in the supernatant using primers specific for the DNA of the DNA-containing organism, thereby forming amplification products specific to the microorganism, and then detecting the amplification products, where their presence indicates that the microorganism is present in the blood or serum of the subject.

DESCRIPTION OF THE PREFERRED EMBODIMENTS

The following examples illustrate the present invention without limitation.

Methods:

1. Serum and Plasma Samples

Whole blood samples were collected in Vacutainer™ tubes containing ethylenediamine tetraacetic acid (EDTA) or other anti-coagulant, such as heparin and oxalate, for obtaining plasma, or whole blood samples were collected without anticoagulant to obtain serum.

2. Sample Preparation

20 µl of serum or plasma were added to 80 µl of a 25 mM NaOH solution containing 0.334 µg/µl calf thymus DNA, and 1.67 double stranded copies per µl of the Internal Positive Control (IPC) plasmid target DNA in a screw-capped microcentrifuge tube. The mixture was vortexed, then heated at 105° C. for five minutes. The samples were allowed to equilibrate to room temperature and centrifuged at 16,000 X g for two minutes at room temperature. 25 µl of the supernatant were added to 75 µl of the PCR reaction admixture (composition described below) and amplified.

3. Polymer Capture—Control

The method of extraction of DNA using polymer capture was carried out as described in Example 3 of U.S. Pat. No 5,582,988, except that 20 µl of serum or plasma were used in the experiments described herein. The DNA-polymer complex was pelleted and the supernatant was discarded (which is expected to contain potential inhibitors of PCR). The DNA was then eluted from the pellet using 100 µl of a 20 mM NaOH solution and heated at 105° C. for 5 minutes, followed by a 2 minute centrifugation step. The supernatant (25 µl) was added to 75 µl of PCR reaction admixture and amplified. The polymer capture procedure was used as a control for comparison with the simplified DNA extraction method of the present invention.

4. PCR Amplification and Detection

The PCR reaction admixture at pH 8.0 contained 160 U/ml of recombinant Taq polymerase, 5.28 µg/ml of TP4-9.2 (a 5 fold excess) and 53.37 µg/ml of TP1-12.2 anti-Taq antibodies, 18 mM Tris buffer, 54 mM potassium chloride, 0.2 µM of each IPC primer (IPC-F1 (forward): Biotin- 5'-CGCCAGCGTGGACCATCAAGTAGTAA-3' <SEQ ID NO.: 1> and IPC-R1 (reverse) 5'-CACGATCCTGGAGCAGACACTGAAGA-3' <SEQ ID NO.: 2>), 0.4 µM of each CMV Assay Specific Primer (LB42M (forward) with the sequence: Biotin-5'-TGCACTGCCAGGTGCTTCGGCTCAT-3' <SEQ ID NO.: 3> and primer LB41 (reverse) 5'-CACCACGCAGCGGCCCTTGATGTTT-3' <SEQ ID NO.: 4>), 1.2 mM total deoxynucleoside triphosphates (dNTPs), 4 mM magnesium chloride, 9.5% glycerol, and a preservative. Typically, the Taq polymerase and anti-Taq antibodies were allowed to pre-incubate at room temperature for 10 minutes, and the $MgCl_2$ was supplied as a separate solution to be added just prior to sample addition. The CMV Assay Specific Primers were designed to be complementary to the DNA encoding the pp65 Matrix Protein of the CMV Late gene in patient specimens. Both the IPC target and CMV pp65 Matrix protein target sequences were cloned into the Bluescript plasmid (Stratagene, La Jolla, Calif.) for use as assay controls. These were accurately quantitated by spectrophotometric analyses and fit to Poisson's distribution. The sequence of the internal positive control target DNA used was: 5'-CGCCAGCGTGGACCATCAAGTAGTAAT-GAACGCACGGACGAGGACATCA TAGAGATTACAC-CTTTATCCACAGTTCTCGGTCTAACG-CAGCAGTCAGTG TATCAGCACCAGCATCCGTAGTGAGTCT-TCAGTGTCTGCTCCAGGATCGT G-3' <SEQ ID NO.: 5>.

25 μl of processed sample were added to 75 μl of the PCR reaction admixture. After addition and mixing, the reaction admixture was introduced into the amplification blister of a plastic PCR pouch containment system (Johnson & Johnson Clinical Diagnostics, Inc., U.S. Pat. Nos. 5,089,233; 5,229, 297; and 5,380,489). . Amplification and detection were carried out using a PCR amplification and detection processing instrument (Johnson & Johnson Clinical Diagnostics, Inc. U.S. Pat. No. 5,567,617). After an initial preheat for 3 minutes at 96° C., the sample was subjected to 40 cycles of amplification, alternating between 96° C. (5 second) denaturations, and 70° C. (40 second) annealing steps. After a 5 minute postheat at 103EC, the amplified products were introduced into the detection chamber of the pouch containing the control and assay specific probes linked to capture beads (Table 1).

TABLE 1

| Bead No. | Designation | Sequence | SEQ ID NO. |
|---|---|---|---|
| Bead 2 | IPC-1P | 5'-CTGCGTTAGACCGAGAACTGTG GATAAAGG-3' | 6 |
| Bead 4 | LBSA-11 (CMV) | 5'-GAACCGAGGGCCGGCTCACCTC TATGTTGG-3' (pp65 Matrix Protein) | 7 |
| Bead 6 | INC-26.7a | 5'-TTAGTAGTAGAAGGACGACGAT GGCG-3' | 8 |

INC-26.7a serves as an Internal Negative Control and is expected to give no signal in a properly functioning PCR pouch.

Color generation on the capture beads was then read visually and compared to a color score card having ten shades of increasing blue color and 15 corresponding numbers ranging from 0 to 10 (0=no signal, 10=high positive signal). A visual score above a 2 indicates a positive test result on that capture bead. In addition, reflectance density ($D_r$) measurements from the PCR processing instrument were recorded. $D_r$ readings above 0. 13 indicate a positive result.

EXAMPLE 1

Extraction of DNA from Plasma Using the Method of the Present Invention: Comparison with Polymer Capture The following experiment was performed to compare the extraction method of the present to the polymer capture method.

Plasma samples from 65 patients were prepared according to the method of the present invention and the polymer capture procedure, as described above. Both 20 μl and 50 μl samples were used in the polymer capture method. These samples all had previously elicited a "No Test" result when evaluated using 50 μl sample volumes prepared by the polymer capture protocol in an initial evaluation. A "No Test" result occurs when the Internal Positive Control capture bead gives a false negative result. The IPC control plasmid that was introduced into the samples was present at 10 copies per final reaction admixture. All prepared samples were combined with the PCR reaction admixture and underwent amplification and detection, as described above.

The "No Test" frequency in polymer capture vs. the method of the invention for plasma samples are summarized in Table 2 below.

TABLE 2

|  | Polymer Capture 50 ΦL sample | Polymer Capture 20 ΦL sample | Invention 20 ΦL sample |
|---|---|---|---|
| IPC Capture Bead Results* | 14/65 | 0/65 | 0/65 |
| "No Test" Frequency | 21% | 0% | 0% |
| Range (Visual Scores) | 3–8 | 3–8 | 5–7.5 |
| Number of samples <4 Visual Score* | 3/65 (4.6%) | 1/65 (1.5%) | 0/65 (0%) |

*number of IPC negative results/total number samples run

The 50 μl polymer capture protocol exhibited a 21% "No Test" frequency whereas the 20 μl polymer capture protocol and the 20 μl protocol of the instant invention had a 0% failure rate. With both polymer capture protocols, there was evidence of reduced signal on some samples and the Internal Positive Control bordered on negative.

Thus, the method of the invention significantly outperformed the 50 μl polymer capture procedure and showed improvement over the 20 μl polymer capture procedure in terms of false negative results on the IPC capture bead. The samples prepared using the 50 μl polymer capture procedure evidently contained inhibitors of PCR or exhibited some other phenomenon associated with polymer capture.

In addition, there was one instance using the 20 μl polymer capture technique where a false positive result on the CMV (LBSA-11) capture bead was obtained from a CMV negative patient sample. As the corresponding 50 μl result was negative (and would have provided 2.5- fold more CMV target DNA from the patient sample if it were truly present), this result exemplifies the complications in a procedure with multiple manipulations, such as product carryover.

EXAMPLE 2

Extraction of DNA from Serum Using the Method of the Present Invention: Comparison with Polymer Capture DNA was extracted from serum samples obtained from 100 CMV IgG-positive, IgM-negative OB/GYN patients provided by Texas Children's Hospital in Houston Tex., using 20 μl of sample in the polymer capture procedure and the method of this invention (see Example 1 above). Prior to sample preparation, CMV control plasmid DNA was added to each sample to yield final single-stranded copy numbers of 20 CMV plasmid targets in the PCR reaction admixture.

The IPC control plasmid also was introduced into the samples at a final level of 10 copies per PCR reaction admixture. All prepared samples were combined with the PCR reaction admixture, as described above. Amplification and detection, as before, were performed in duplicate in PCR pouches.

The frequency of false negative results in polymer capture versus the method of the invention using serum are summarized in Table 3 below.

TABLE 3

|  | Polymer Capture 20 ΦL sample | Method of the Present Invention 20 ΦL sample |
| --- | --- | --- |
| CMV Capture Bead Results* (% Frequency) | 5/100 (5%) | 0/100 (0%) |
| IPC Capture Bead Results* (% Frequency) | 0/100 (0%) | 0/100 (0%) |

*number of IPC negative results/total number samples run

Neither sample preparation procedure gave negative results on the IPC capture bead. However, addition of CMV plasmid target to the samples resulted in a 5% false negative frequency on the CMV bead when the polymer capture method was used, indicating potential inhibition of PCR By contrast, there were no false negative CMV bead results using the method of the present invention.

EXAMPLE 3

Extraction of DNA from Plasma from a CMV Patient Population Using the Method of the Present Invention: Comparison with GeneClean II Sample The following experiment was performed to test the efficacy of the method of the present invention in extracting DNA from patient samples.

Plasma samples were either (i) extracted using the Gene Clean II method (Bio 101, Inc.) and characterized using both a very sensitive $p^{32}$ liquid hybridization CMV PCR assay and a direct gel CMV PCR assay or (ii) extracted using the method of the present invention and assayed as described in Example 1 above. The IPC control plasmid, which was introduced into each sample, was present at 25 double strand copies per final reaction admixture. All samples were combined with the PCR reaction admixture followed by amplification and detection in duplicate in PCR pouches, as above.

The results are on the CMV capture bead are shown in Table 4 below.

TABLE 4

The Method of the Present Invention vs. GeneClean II Sample Preparation of Plasma Samples

|  |  | GeneClean + | GeneClean − |
| --- | --- | --- | --- |
| Present Invention | + | 10 | 3 |
|  | − | 2 | 10 |

All positive TCH plasma samples were considered to be very low positive samples, as all were positive only by the liquid hybridization assay and were negative on direct gel, which is indicative of a low copy level of CMV in the sample.

There was an 80% concordance between the two sample preparation methods. Using the method of the present invention, 10 of the 12 samples gave positive results by the GeneClean method and two gave negative results. Upon retesting the sample preparations, of the original two false negative samples, one became positive. For the GeneClean negative plasma samples, a similar situation was encountered. With the 13 negative samples, both sample preparation methods gave concordant results for ten of the specimens (the same 10).

In addition, there were three instances where the method of the present invention indicated a CMV positive sample. Upon retesting the sample preparations, two of these three samples again indicated a CMV positive result. Because of its inherent sensitivity, this is a common observation in PCR assays, where very low target samples give discrepant results. This is predicted based on an expected Poisson sampling distribution.

EXAMPLE 4

Addition of Potentially Interfering Substances Added to Plasma

The following experiment was performed to test the ability of the method of the invention to remove potentially interfering substances from plasma.

Normal plasma sample pools were treated to vary the pH and add blood sample collection additives, and other substances known or suspected of being capable of interfering with sample preparation, amplification, or detection. The compounds were added to a sample at three times the estimated peak serum level (Table 5).

DNA was extracted from 20 μl of each sample using the method of the present invention and the prior art polymer capture method, as described in Example 1 above. The IPC and CMV plasmids were present at 25 and 10 double strand copies, respectively, per final PCR reaction admixture. Half of the samples contained only the IPC plasmid to evaluate false positive results (color up on the CMV probe bead) that could arise due to sample cross-contamination or product carryover. All samples were combined with the PCR reaction admixture followed by amplification and detection in PCR pouches. For each compound, four pouches were run for both the 0 and the 10 CMV copy levels. In addition, the appropriate controls were run containing the various solvents (water, acetone, ethyl alcohol) used in preparing the compounds for inclusion in the assay.

TABLE 5

| Interference Evaluated | Rationale | Peak Serum Levels (in Φg/mL) | Polymer Capture Result* | Invention * |
| --- | --- | --- | --- | --- |
| Acetaminophen | Common drug | 20 | + | + |
| Amoxicillin | Common drug | 10 | + | + |
| Aspirin | Common drug | 35 | + | + |
| Codeine | Common drug | 0.4 | + | + |
| Dextromethorphan | Common drug | 0.38 | + | + |
| Furosemide (Lasix) | Common drug | 10 | + | + |
| Ibuprofen | Common drug | 70 | + | + |
| Phenytoin (Dilantin) | Common drug | 20 | + | + |
| Prednisone | Common drug | 0.1 | + | + |

TABLE 5-continued

| Interference Evaluated | Rationale | Peak Serum Levels (in Φg/mL) | Polymer Capture Result* | Invention * |
|---|---|---|---|---|
| Acetyl cysteine | Detection interferent | 300 | + | + |
| Ascorbic Acid | Detection interferent | 20 | + | + |
| Dipyrone | Detection interferent | 200 | + | + |
| Dopamine | Detection interferent | 100 | + | + |
| EDTA - 0.25x draw | Sample collection additive | 1500 | + | + |
| Gentisic acid | Detection interferent | 55 | + | + |
| Heparin (Na) - 0.25x draw | Sample collection additive | 33.3 | + | + |
| Hypaque | Detection interferent | 500 | + | + |
| Levodopa | Detection interferent | 4 | + | + |
| Oxalate - 0.25x draw | Sample collection additive | 2000 | + | + |
| Cocaine (as Benzoylecgonine) | Drug of abuse | 1 | + | + |
| Ethyl alcohol | Drug of abuse | 1320 | + | + |
| Heroin (as Morphine sulfate) | Drugs of abuse | 0.135 | + | + |
| Methadone | Drugs of abuse | 0.5 | + | + |
| Methamphetamine | Drugs of abuse | 0.5 | + | + |
| THC | Drug of abuse | 0.1 | + | + |
| Albumin | High concentration analyte | 50000 | + | + |
| Whole Blood | Residual blood in serum/plasma | 25% of sample volume | 2 NT & 3IPC FN | + |
| Bilirubin (total) | Neonates <1 week old | 120 | + | + |
| Creatinine | Renal failure patients | 15 | + | + |
| Ca(NO$_3$)$_2$ | High concentration analyte | 104 | + | + |
| Cyclosporin A | Transplant patients | 1 | + | + |
| Glucose | High concentration analyte | 1000 | + | + |
| Lipemic (as Cholesterol) | High concentration analyte | 1000 | + | + |
| MgCl$_2$ | Test for PCR inhibition | 190 | + | + |
| Low pH (6.8) | Test for PCR inhibition | sample pH'd | 1 FP | + |
| High pH (8.8) | Test for PCR inhibition | sample pH'd | + | + |
| Zn(OAc)$_2$ | Test for PCR inhibition | 1.5 | + | + |
| Foscarnet | CMV Drug | 180 | + | + |
| Ganciclovir | CMV Drug | 1.18 | + | + |
| Crixivan | HIV Drug | 8.98 | + | + |
| ddC (Hivid) | HIV Drug | 0.0252 | + | + |
| ddI (Videx) | HIV Drug | 1.6 | + | + |

Key:
* +indicates positive results on all CMV and IPC capture beads where targets are present;
FP = False Positive;
FN = False Negative (CMV negative result on expected CMV positive capture bead where CMV was input at 10 copy level);
NT = "No Test" IPC capture bead is Negative on an expected CMV Negative sample (CMV=Neg);

During initial testing there were a few sporadic false negative results on both the CMV and IPC capture beads and several "No Test" results for each of the sample preparation methods, although they were predominantly seen on polymer capture samples. In addition, several of the controls gave unexpected negative results and there were indications of pouch failures contributing to these.

Upon retesting the previously prepared samples, all results for all substances tested elicited positive results for both the polymer capture and the method of the present invention, with the exception of the 25% blood samples (25 parts by volume of whole blood added to 75 parts by volume of the plasma prior to DNA extraction) prepared using the polymer capture method. Two of the four samples containing only IPC target (no CMV target) again showed "No Test" results on the IPC capture bead. Also, three of the four samples containing both the IPC and CMV target DNA's showed inhibition on the IPC capture bead, with visual scores of only "1." For two of these, the CMV capture bead also indicated signs of inhibition (visual color scores of "3" and "4"). Also, there was again one instance of a false positive result using the polymer capture technique (at the low pH variation) again indicating the need for a simple procedure with a minimum number of steps to prevent carryover contamination.

These results indicate that 25% whole blood is inhibitory in the HCMV assay when samples were prepared using the polymer capture technique. By contrast, extraction of DNA using the method of the present invention resulted in no inhibition of PCR amplification and detection. This is significant because serum and plasma samples in clinical laboratories are often contaminated with red blood cells. Furthermore, the polymer capture technique is more laborious and permits greater exposure of the sample to the environment compared with the method of the instant invention which compares favorably with polymer capture.

DNA extraction using the method of this invention does not result in inhibition of PCR amplification or detection of amplified products with any of the tested substances. This simple method represents a significant advance over more cumbersome, time consuming and laborious methods of the prior art.

All patents, applications, articles, publications, and test methods mentioned above are hereby incorporated by reference in their entirety.

Many variations of the present invention will suggest themselves to those skilled in the art in light of the above detailed description. Such obvious variations are within the full intended scope of the appended claims.

What is claimed is:

1. A method for extracting DNA from serum or plasma, said method comprising:

(i) contacting serum or plasma with alkali to yield alkalinized serum or plasma;

(ii) heating said alkalinized serum or plasma to a temperature ranging from about 100 to about 110° C. for a time ranging from about 5 to about 20 minutes to yield heated alkalinized serum or plasma;

(iii) centrifuging said heated alkalinized serum or plasma to yield a DNA-containing supernatant; and (iv) recovering said DNA-containing supernatant.

2. A method as defined in claim 1, wherein after said heating step (ii) and prior to said centrifuging step (iii), said heated alkalinized serum or plasma is cooled or allowed to cool to about 25° C.

3. A method as defined in claim 2, wherein said alkali is sodium hydroxide.

4. A method as defined in claim 2, wherein said temperature is about 105° C.

5. A method as defined in claim 2, wherein said time is about 5 minutes.

6. A method as defined in claim 2, wherein said centrifuging is at about 16,000 x g for about 2 minutes.

7. A method as defined in claim 2, wherein said alkalinized serum or plasma comprises alkali at a concentration ranging from about 15 to about 50 mM.

8. A method for detecting a DNA-containing microorganism in serum or plasma, said method comprising:

(i) contacting serum or plasma from a subject with alkali to yield alkalinized serum or plasma;

(ii) heating said alkalinized serum or plasma to a temperature ranging between about 100 to about 110° C. for a time ranging from about 5 to about 20 minutes to yield heated alkalinized serum or plasma;

(iii) centrifuging said heated alkalinized serum or plasma to yield a DNA-containing supernatant;

(iv) recovering said DNA-containing supernatant;

(v) subjecting said DNA in said supernatant to amplification using oligonucleotide primers that recognize sequences within the DNA of said DNA-containing microorganism, to form amplification products specific to said DNA-containing microorganism; and (vi) detecting said amplification products, wherein detection of said amplification products indicates the presence of said microorganism in said serum or plasma.

9. A method as defined in claim 8, wherein after said contacting step (ii) and prior to said centrifuging step (iii), said heated alkalinized serum or plasma is cooled or allowed to cool to about 25° C.

10. A method as defined in claim 8, wherein said temperature is about 105° C.

11. A method as defined in claim 8, wherein said microorganism is a bacteria.

12. A method as defined in claim 8, wherein said microorganism is a virus.

13. A method as defined in claim 12, wherein said virus is human cytomegalovirus.

14. A method as defined in claim 8, wherein said alkalinized serum or plasma comprises alkali at a concentration of about 20 mM.

15. A method for extracting DNA from serum or plasma, which method consists of steps of:

(a) contacting serum or plasma with alkali to yield aklalinized serum or plasma;

(b) heating said alkalinized serum or plasma to a temperature ranging from about 100 to about 110° C. for a time ranging from about 5 to about 20 minutes to yield heated alkalinized serum or plasma;

(c) centrifuging said heated alkalinized serum or plasma to yield a DNA-containing supernatant; and (d) recovering said DNA-containing supernatant.

16. A method for detecting a DNA-containing microorganism in serum or plasma, which method consists of steps of:

(a) contacting serum or plasma from a subject with alkali to yield alkalinized serum or plasma;

(b) heating said alkalinized serum or plasma to a temperature ranging between about 100 to about 110° C.

for a time ranging from abut 5 to about 20 minutes to yield heated alkalinized serum or plasma;

(c) centrifuging said heated alkalinized serum or plasma to yield a DNA-containing supernatant;

(d) recovering said DNA-containing supernatant;

(e) subjecting said DNA in said supernatant to amplification using oligonucleotide primers that recognize sequences within the DNA of said DNA-containing microorganism, to form amplification products specific to said DNA-containing microorganism; and (f) detecting said amplification products, wherein detection of said amplification products indicates the presence of said microorganism in said serum or plasma.

* * * * *

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 1
cgccagcgtg gaccatcaag tagtaa                                              26

<210> SEQ ID NO 2
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 2
cacgatcctg gagcagacac tgaaga                                              26

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 3
tgcactgcca ggtgcttcgg ctcat                                               25

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 4
caccacgcag cggcccttga tgttt                                               25

<210> SEQ ID NO 5
<211> LENGTH: 147
<212> TYPE: DNA
<213> ORGANISM: Artificial Sequence
<220> FEATURE:
<223> OTHER INFORMATION: target nucleic acid for an internal positive
      control

<400> SEQUENCE: 5
cgccagcgtg gaccatcaag tagtaatgaa cgcacggacg aggacatcat agagattaca         60
cctttatcca cagttctcgg tctaacgcag tcagtgtatc agcaccagca tccgtagtga        120
gtcttcagtg tctgctccag gatcgtg                                            147

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 6

-continued

```
ctgcgttaga ccgagaactg tggataaagg                                30

<210> SEQ ID NO 7
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 7
gaaccgaggg ccggctcacc tctatgttgg                                30

<210> SEQ ID NO 8
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 8
ttagtagtag aaggacgacg atggcg                                    26
```